Figure 1:
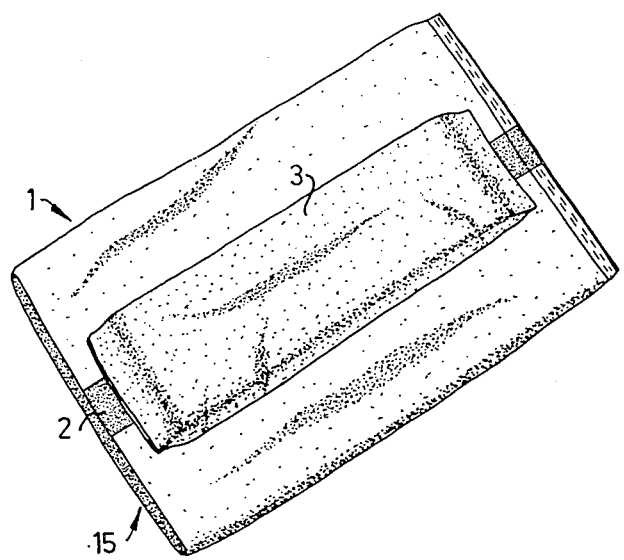

United States Patent [19]

Fröidh et al.

[11] Patent Number: 4,765,477
[45] Date of Patent: Aug. 23, 1988

[54] PACKAGE FOR INDIVIDUAL, DISPOSABLE SANITARY ARTICLES AND A METHOD OF MANUFACTURING SUCH A PACKAGE

[75] Inventors: Arne Fröidh, Stenungsund; Stewe Alsenvik; Urban Widlund, both of Mölnlycke; Carl-Daniel Norenberg, Göteborg, all of Sweden

[73] Assignee: Molnycke AB, Gothenburg, Sweden

[21] Appl. No.: 802,212

[22] Filed: Nov. 26, 1985

[30] Foreign Application Priority Data

Nov. 26, 1984 [SE] Sweden .................. 8405953

[51] Int. Cl.⁴ .................. B65D 81/00; B65D 85/16
[52] U.S. Cl. .................. 206/438; 206/460; 383/4; 604/358
[58] Field of Search .................. 53/461, 463, 469; 206/438, 460, 440, 363; 383/4; 604/385.1, 385.2, 358, 393, 397, 402

[56] References Cited

U.S. PATENT DOCUMENTS

| | | |
|---|---|---|
| 2,952,354 | 9/1960 | Whitelaw et al. .................. 206/440 |
| 3,035,578 | 5/1962 | Elmore .................. 206/440 |
| 3,369,657 | 2/1968 | Quade . |
| 3,490,576 | 1/1970 | Alessi et al. .................. 206/820 |
| 3,652,006 | 3/1972 | Trewella .................. 206/440 |
| 3,865,110 | 2/1975 | Traverse . |
| 3,877,432 | 4/1975 | Gellert .................. 604/385.1 |
| 3,973,567 | 8/1976 | Srinivasan et al. .................. 206/440 |
| 4,203,520 | 5/1980 | Schuster .................. 206/439 |
| 4,493,713 | 1/1985 | Izzo .................. 604/385.1 |
| 4,556,146 | 12/1985 | Swanson et al. .................. 206/440 |

FOREIGN PATENT DOCUMENTS 0560879 4/1944 United Kingdom .
2051579 1/1981 United Kingdom .

Primary Examiner—Jimmy G. Foster

[57] ABSTRACT

A package for disposable sanitary articles such as sanitary napkins, incontinence products and the like, in which for each single article there is provided a wrapper formed of a bag-shaped package blank which, with the article applied to one of its outsides, is folded around the article. After the article is used, what was originally the wrapper is usable as a bag in which to dispose of the used article.

5 Claims, 2 Drawing Sheets

PACKAGE FOR INDIVIDUAL, DISPOSABLE SANITARY ARTICLES AND A METHOD OF MANUFACTURING SUCH A PACKAGE

The present invention relates primarily to a package for disposable sanitary articles such as sanitary napkins, incontinence articles and the like, and secondly to a method of producing such a package.

Up to now, disposable articles such as diapers, sanitary napkins and the like have generally been loosely packed in large packages such as plastic bags and cartons. When travelling, packages of this type are of course impractical and too bulky in case only a small number of such articles would be required. For this reason there have lately been developed one-piece packages for this kind of sanitary articles. A one-piece package of this type is described in German Laid-open Publication No. 31 46 067 and consists of a plastic film or the like having one end portion folded in over its center portion, the side edges of these portions, brought into alignment as a result of the folding, being welded together to form a collecting pocket into which a folded disposable article can be inserted. The opposite end portion of the packing film is adapted to serve as a sealing cover over said pocket, this portion as well being welded along its edges to the edges of said pocket. The cover thus created is furthermore provided with an adhesive bead by means of which the pocket can be resealed after the package has been opened.

This one-piece package also has for its purpose to constitute a so-called service bag, i.e. a collecting bag for the used disposable article.

Since disposable articles in the form of diapers, sanitary napkins and the like will change their shape and become wet and clumsy after the absorption of body fluids, it will be practically impossible to tuck down a used article of the kind in question into this type of prior art packaging and/or service bag.

For this reason there exists a great demand for enabling disposable articles to be packed in one-piece packages, which after use of the article contained therein could also be utilized as service bags for storage of the used article. However, moisture absorbing disposable articles are relatively bulky, and in the packaging process it is of course necessary therefore to keep the packages as compact as possible. So far however, this object has been impossible to combine with the demand of making the packages large enough to be usable as service bags for such articles.

The problems defined above have however been completely eliminated with the present invention in that a package in accordance therewith is primarily distinguished in that the package blank has the form of a bag which, when the article to be packed is applied to one of its outsides, is folded around said article in an openably sealed condition as a tight all-over enclosure for producing the package, said bag possibly being folded-over along with the article, and in that after the package has been opened, the bag is adapted to be utilized as a service bag for a used article. After this compact package has been opened, there is thus obtained a bag which is large enough for accommodating a used article.

In the following there is revealed, in addition to some suitable embodiments of a package made according to the invention, a method of producing a package of this type which has proved especially simple and advantageous.

Figure 2:
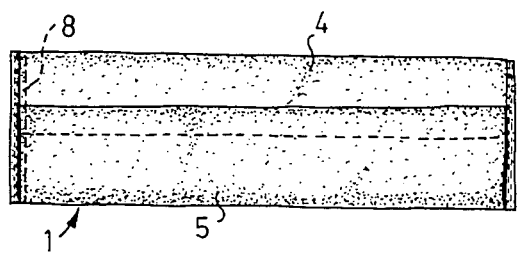

The invention will be described in more detail below with reference to the accompanying drawings, of which FIG. 1 is a perspective view of a bag-shaped package blank having applied to one of its outsides an absorption article in the form of a disposable sanitary napkin, FIG. 2 is a plan view of the embodiment of FIG. 1 in a sealed condition, and FIGS. 3-5 finally show how a second embodiment of a package made according to the invention can be accomplished.

As can be seen from the drawings, a package blank in the form of a liquid impervious plastic bag 1 has a central zone 2, located on one of its outsides, to which there is applied a release agent such as silicone for example, whereby a disposable sanitary article such as a sanitary napkin 3 for example, consisting of an absorption body enclosed by a casing, is attached to the outside of the bag-shaped package blank coated with release agent. On its outside facing away from the wearer, said napkin is provided with one or more binder beads, preferably hot melt beads, for the purpose of keeping the napkin properly placed in the underpants of the wearer during use. These adhesive beads, not shown here, are utilized in a package made according to the invention for securing the napkin to the region 2 of the bag-shaped package blank coated with release agent. As is especially clearly indicated in FIG. 3, the package blank or bag 1 extends with lateral portions 4,5 along either side of the napkin attached to the blank or bag, and with end portions 6,7 beyond the two end edges of the napkin.

In order to enclose the napkin 3, as shown in FIG. 2, the extended lateral portions 4 and 5 of the package blank or bag 1 are folded around the napkin with overlapping edges, and are fixed by welding at both ends thereof. In this connection there is suitably arranged a perforation 8 inside the end weld at the initially open end 15 of the blank or bag. When the napkin 3 is taken out, this perforation will break open whereupon the bag 1, utilized as a package blank or wrapping, is automatically opened. Prior to wrap-over folding and welding, the bag 1 may possibly be coated wtih a release agent applied along its bottom edge on its outside to which the napkin 3 is fixed whereby the weld, made at the bottom edge 7 for sealing the bag around the napkin, will be easily openable.

Figure 3:
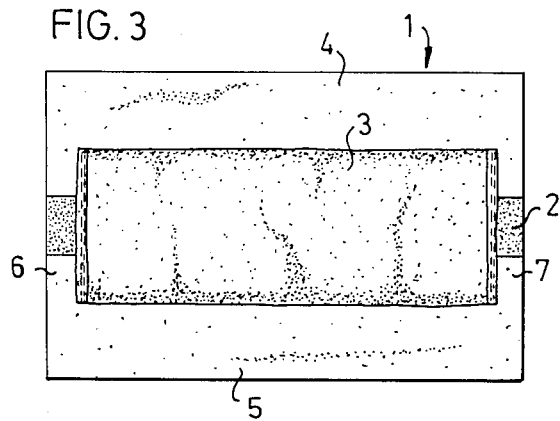

FIG. 3 illustrates a sanitary napkin 3, located on the outside of a bag-shaped blank 1 having a somewhat narrower lateral dimension in comparison with the embodiment shown in FIGS. 1 and 2. More exactly, the napkin 3 is fixed with its back coated with binding agent to an outside of the blank or bag 1 which, within the area of attachment, is coated with release agent 2.

Figure 4:
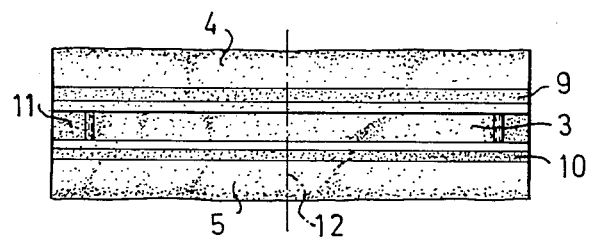

As shown in FIG. 4, the side portions 4,5 of the package or bag 1 extending beyond the napkin 3 are first folded over the two longitudinal side edges of the napkin and a distance in over it, the two folded-over side portions not overlapping each other there. Adhesive beads 9,10 are then applied to the folded-over bag portions extending along the napkin, hot melt 11 suitably being applied at the same time in the gap between the foldedover side portions 4,5 at the center of the end portion 6.

Figure 5:
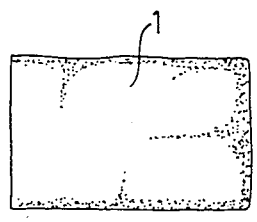

In order to form a package of the kind disclosed in FIG. 5 and intended to be sealed around the napkin 3, the unit shown in FIG. 4 is folded along a transverse center line 12, the unit thus folded being held together by means of the binder beads designated by numerals 9, 10 and 11 in FIG. 4.

The embodiment of a package in accordance with the invention as shown in FIG. 5 can be opened by tearing along the binder beads 9,10,11 the adhering capacity of which is adaptable to a suitable degree.

The invention is not restricted to the embodiments described above, but a plurality of modifications are conceivable within the scope of the patent claims. For example, sealing of the disposable absorbent article can be performed in a number of different ways. The essential feature of the invention is that the article subjected to wrapping be applied to the outside of a bag-shaped package blank, which is subsequently utilized as a wrapper for the article.

In the production of packages according to the invention the starting material can be a plastic hose, for example, onto the exterior of which articles to be packed are applied at uniformly spaced intervals. The hose is then folded around the articles and welded, perforated and/or cut off between each individual article in order to obtain detached one-piece parcels, or a continuous row of such parcels, which row can be folded or rolled up to form a suitable large-size package comprised of one-piece parcels.

We claim:

1. A packaged individual disposable sanitary article, comprising a bag formed of two layers of material joined along opposite sides and along at least one end, the bag having two major outer surfaces comprised by the sides of said layers which are remote from each other, a said sanitary article disposed on one of said outer surfaces, the bag being folded over the sanitary article and sealed, the bag when unfolded having a width greater than the width of the sanitary article and a length greater than the length of the sanitary article, the portions of the bag of greater width than the article being folded over the article and the portions of the bag of greater length than the article being sealed together.

2. A packaged article as claimed in claim 1, and perforations along one of said sealed-together portions of the bag endwise beyond the sanitary article.

3. A packaged article as claimed in claim 1, and release means releasably holding the sanitary article to said one surface of the bag.

4. A packaged individual disposable sanitary article, comprising a bag formed of two layers of material joined along opposite sides and along at least one end, the bag having two major outer surfaces comprised by the sides of said layers which are remote from each other, a said sanitry article disposed on one of said outer surfaces, the bag being folded over the sanitary article and sealed, the width of said bag when unfolded being greater than the width of said sanitary article and the length of said bag when unfolded being greater than the length of said sanitary article, the portions of the bag of greater width being folded over the sanitary article and having adhesive on the outer edges of the thus-folded-over portions, the package being folded double about a line transverse to the length of the sanitary article and disposed midway of the length thereof whereby portions of said adhesive-coated edges on opposite sides of said line adhere to each other.

5. A packaged article as claimed in claim 4, there being adhesive on those portions of the bag that extend endwise beyond the sanitary article, this latter adhesive holding the ends of the folded-over package article together.

* * * * *